(12) United States Patent
Heuser et al.

(10) Patent No.: US 9,301,830 B2
(45) Date of Patent: Apr. 5, 2016

(54) DIFFERENTIAL DILATION STENT AND METHOD OF USE

(75) Inventors: Richard R. Heuser, Phoenix, AZ (US); Kumar G. Jambunathan, Sunnyvale, CA (US); Richard A. Lotti, Santa Cruz, CA (US)

(73) Assignee: PQ Bypass, Inc., Sunnyvale, CA (US)

( * ) Notice: Subject to any disclaimer, the term of this patent is extended or adjusted under 35 U.S.C. 154(b) by 0 days.

(21) Appl. No.: 13/422,594

(22) Filed: Mar. 16, 2012

(65) Prior Publication Data

US 2012/0239137 A1 Sep. 20, 2012

Related U.S. Application Data (60) Provisional application No. 61/453,876, filed on Mar. 17, 2011.

(51) Int. Cl.
  *A61F 2/06* (2013.01)
  *A61F 2/07* (2013.01)
  *A61F 2/89* (2013.01)

(52) U.S. Cl.
  CPC ... *A61F 2/07* (2013.01); *A61F 2/89* (2013.01); *A61F 2002/072* (2013.01); *A61F 2250/0018* (2013.01); *A61F 2250/0039* (2013.01)

(58) Field of Classification Search
  USPC ........... 623/1.11, 1.15, 1.16, 1.44, 1.17, 1.18, 623/1.2
  See application file for complete search history.

(56) References Cited

U.S. PATENT DOCUMENTS

| | | | |
|---|---|---|---|
| 5,800,515 A | 9/1998 | Nadal et al. | |
| 5,843,167 A * | 12/1998 | Dwyer et al. | 623/1.14 |
| 6,042,605 A | 3/2000 | Martin et al. | |
| 7,041,127 B2 | 5/2006 | Ledergerber | |
| 7,090,649 B2 * | 8/2006 | Kang | 601/2 |
| 7,300,459 B2 | 11/2007 | Heuser | |
| 7,803,181 B2 | 9/2010 | Furst et al. | |
| 2001/0034550 A1 * | 10/2001 | Buirge et al. | 623/1.47 |
| 2004/0143318 A1 * | 7/2004 | Tseng et al. | 623/1.16 |
| 2005/0234546 A1 * | 10/2005 | Nugent et al. | 623/2.11 |

(Continued)

FOREIGN PATENT DOCUMENTS

| | | |
|---|---|---|
| EP | 0815806 A2 | 1/1998 |
| WO | WO 98/34668 A1 | 8/1998 |

OTHER PUBLICATIONS

International search report and written opinion dated Jul. 13, 2012 for PCT/US2012/029543.

(Continued)

*Primary Examiner* — Thomas J. Sweet
*Assistant Examiner* — Tiffany Shipmon
(74) *Attorney, Agent, or Firm* — Wilson Sonsini Goodrich & Rosati (57) ABSTRACT

Embodiments herein provide differential dilation stents for use in percutaneous interventions, such as transluminal bypass procedures. In some embodiments, the stents may be used in the process of creating an arteriovenous (AV) fistula during a percutaneous bypass procedure, and such stents may have two or more specialized regions that are configured to adopt a predetermined diameter, shape, and/or tensile strength upon insertion in order to suit the needs of the vessel or procedure. The disclosed stents may be used for creating and/or maintaining an arterial/venous fistula for bypass of an occlusion in a cardiac artery using a cardiac vein, or the femoral artery, for example using the tibial or popliteal vein.

17 Claims, 5 Drawing Sheets

(56) References Cited

U.S. PATENT DOCUMENTS

| | | |
|---|---|---|
| 2007/0038176 A1* | 2/2007 | Weber et al. ............... 604/93.01 |
| 2007/0179590 A1 | 8/2007 | Lu et al. |
| 2007/0191927 A1* | 8/2007 | Bowe et al. .................. 623/1.15 |
| 2007/0207186 A1* | 9/2007 | Scanlon et al. ............... 424/424 |
| 2008/0262604 A1* | 10/2008 | Stengel ........................ 623/1.31 |
| 2008/0300674 A1* | 12/2008 | Jang ............................. 623/1.16 |
| 2009/0171465 A1 | 7/2009 | Bucay-Couto et al. |

OTHER PUBLICATIONS

European search report and opinion dated Dec. 4, 2014 for EP Application No. 12757199.0.

* cited by examiner

DIFFERENTIAL DILATION STENT AND METHOD OF USE

CROSS-REFERENCE TO RELATED APPLICATIONS

This application claims the benefit of provisional application 61/453,876, filed on Mar. 17, 2011, the full disclosure of which is incorporated herein by reference.

BACKGROUND OF THE INVENTION

1. Field of the Invention

Embodiments herein relate to methods and devices for connecting adjacent blood vessels, e.g., an artery and an adjacent vein, to adapt the vein for arterial blood flow, and more particularly, embodiments relate to devices such as differential dilation stents for creating and maintaining a pathway between an artery and a vein to form a fistula connecting the blood vessels.

The superficial femoral arteries and the popliteal arteries are leg arteries that provide blood flow through the legs and to the feet, particularly to the skin and areas just below the skin. Patients suffering from partial or complete occlusions in such arteries typically experience claudication (e.g., leg pain or limping while walking) and difficulty in healing wounds on the legs due to ischemia, although the deep femoral artery may provide enough circulation that at least the pain is reduced by resting. However, standard open bypass often is impossible on such patients, particularly those with diabetes-narrowed arteries, because of the substandard ability to heal the necessary incisions. Neither performing angioplasty nor inserting stents is likely to help where the vessels are too small or the occlusion extends all the way down to the foot. In severe cases, non-healing ulcers or resting pain may leave no alternative except amputation. Thus, peripheral vascular disease presents a serious health risk.

2. Description of the Background Art

Commonly assigned and invented U.S. Pat. No. 7,300,459 describes a stent with a covering that can be differentially dilated.

SUMMARY OF THE INVENTION

The present invention provides stents suitable for implantation in human blood vessels, including both arteries and veins. The stents are typically in the form of a stent-graft including an inner scaffold member, typically formed from a metal structure such as a cylindrical mesh body having an inside surface and an outside surface. The cylindrical mesh body or other scaffold component will be covered, preferably over both the inside and outside surfaces, with a flexible coating which may comprise a polytetrafluoroethylene (PTFE material), such as electrospun PTFE, an ultra high molecular weight polyethylene (UHMWPE material), or the like. In both cases, the coating material will typically be in the form of a thin membrane or sheet, and small holes, such as laser-drilled holes, may be formed through the material in order to promote cellular in-growth. Such holes will typically have a diameter in the range from 5 microns to 30 microns. The inner stent or scaffold component may be formed from either balloon-expandable materials and self-expandable materials. Preferably, however, the stent or scaffold will be in the form of a super elastic metal, such as nickel titanium alloy.

In particular embodiments, the stent or scaffold body will be formed or treated to include at least two regions having different strengths, particularly having greater or lesser hoop strengths. It has been found that providing the regions near each end of the stent with a greater hoop strength than the region(s) in the middle is useful when stents are deployed between blood vessels, where the end pass through openings between the blood vessels that can provide relatively high compressive forces which can collapse the stents or stent-grafts. Usually a region between the reinforced which passes through a vein will have a diameter less than that of the vein to allow continuous venous blood flow after the bypass is in place. Thus, exemplary stents and stent-grafts can have a first region with a high tensile strength or hoop strength and a diameter selected to extend across the arterial lumen proximal to the occlusion, a second region with a lesser tensile or hoop strength and a diameter usually less than that of the vein adjustment to the arterial occlusion, and finally at least a third region having a greater tensile or hoop strength than the second region and a diameter selected to extend fully across the arterial lumen distal to the occlusion. These regions are preferably arranged with higher strength regions at each end and the lower strength region between said ends.

Exemplary dimensions for the stents and strent-grafts of the present invention include a length from a proximal end to a distal end of the stent or stent-graft from 40 cm to 150 cm. With such lengths, the first region will typically have a diameter from about 4 mm to 9 mm, and a length from 10 cm to 20 cm. The second region will have a diameter from about 6 mm to 11 mm and a length in the range from about 25 cm to 45 cm. The third region will have a diameter in the range from 2 mm to 6 mm and a length in the range from 15 cm to 25 cm. These dimensions are particularly suitable for placing the stent from a femoral artery, into an adjacent femoral vein and/or poplitel vein, back into the femoral artery, typically to bypass an occlusion.

In other embodiments, the distance from the proximal end to the distal end may be in the range from 35 cm to 45 cm, where the first region has a diameter from 6 mm to 8 mm and the third region has a diameter from 4 mm to 6 mm. In yet another embodiment, the distance from the proximal end to the distal end is about 40 cm and the first region has a diameter of 7 mm and the third region has a diameter of about 5 mm. In yet another embodiment, the distance from the proximal to distal end of the stent is in the range from 55 cm to 65 cm in the first region, has a diameter in the range from 5 mm to 7 mm and the third region has a diameter from 2 mm to 4 mm. In yet another embodiment, the distance from the proximal end to the distal end of the stent is about 60 cm. The first region has a diameter of about 6 mm and the third region has a diameter of about 3 mm.

In other specific embodiments, the mesh body or other stent scaffold may be pre-formed or biased to have at least one curve, optionally including a single S-shaped curve, and further optionally including a pair of S-shaped curves which are arranged with the first curve located near a proximal end of the stent and a second curve located near a distal end of the stent.

In particular designs of the stents of the present invention, the mesh body or scaffold will comprise a plurality of serpentine rings arranged in a longitudinally successive pattern. Each serpentine ring will include elongate struts joined by arcuate joints, and the adjacent rings will themselves be arranged in a generally continuous helical pattern (resembling a helical ribbon wrapped over a cylinder) with a helical gap between the adjacent ends of each ring.

In a first specific embodiment, at least one of the two terminal serpentine rings will have a tail wire, which is attached along its length to an adjacent strut. Such a structure can minimize loading and movement of the tail wire relative to the cover material of the stent. In a specific embodiment, the adjacent strut which is attached to the tail wire can itself extend in to a second and even a third ring moving inwardly from the terminal end with such an elongated stent being further attached to the second and optionally third adjacent serpentine ring.

In other preferred embodiments of the scaffold or cylindrical mesh body, a longitudinal gap will be maintained between at least most of the opposed ends of adjacent arcuate joints. In particular, if a helical line is drawn between circumferentially adjacent arcuate joints on a first serpentine ring, and a second helical line drawn on the opposed ends of the immediately adjacent serpentine ring, then these first and second helical lines will maintain a minimum separation, typically in the range from 0.01 inch (0.25 mm) to 0.05 inches (1.25 mm), frequently being about 0.025 inches. Such caps allow the stent to accommodate a tight bending radius, typically of at least 0.6 inches (15 mm). While a larger gap would allow for even tighter bending, a gap in the range set forth above will provide both a desired radial strength and a desired bendability.

Additionally, the adjacent arcuate joints will usually be circumferentially offset so that the joint on one serpentine ring will be aligned with the gap between joints on the adjacent serpentine ring. Such "out-of-phase" joints reduce wear and interference which might occur if the joints were aligned so that they would interfere (collide) with each other when the stent is bent.

In still other aspects of the present invention, the flexible coating will comprise at least one sheet or membrane on each side of the scaffold or cylindrical mesh body structure in order to fully encapsulate the scaffold structure. Additionally, it will often be preferred to cut-out or "scallop" the end of the flexible coating to match the undulations of the terminal serpentine ring. Further, it will frequently be desirable to coat the flexible coating with a drug, such as heparin, on the outer surface, the inner surface, or both.

BRIEF DESCRIPTION OF THE DRAWINGS

Embodiments will be readily understood by the following detailed description in conjunction with the accompanying drawings. Embodiments are illustrated by way of example and not by way of limitation in the figures of the accompanying drawings.

DETAILED DESCRIPTION OF THE INVENTION

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous.

Embodiments herein provide differential dilation stents for use in percutaneous interventions, such as peripheral transluminal bypass procedures. In some embodiments, the stent may be used in the process of creating an arteriovenous (AV) fistula during a percutaneous bypass procedure, and such stents may have two or more specialized regions that are configured to adopt a predetermined diameter, shape, and/or tensile strength upon insertion in order to suit the needs of the vessel or procedure. An example of such a procedure is described herein for a bypass in a generic artery, but one of skill in the art will recognize that the approach may be adapted for use in the treatment for peripheral vascular disease in any peripheral artery, such as in an iliac artery, superficial femoral artery, common femoral artery, popliteal artery, posterior tibial artery, perineal artery, or anterior tibial artery.

Figure 1:
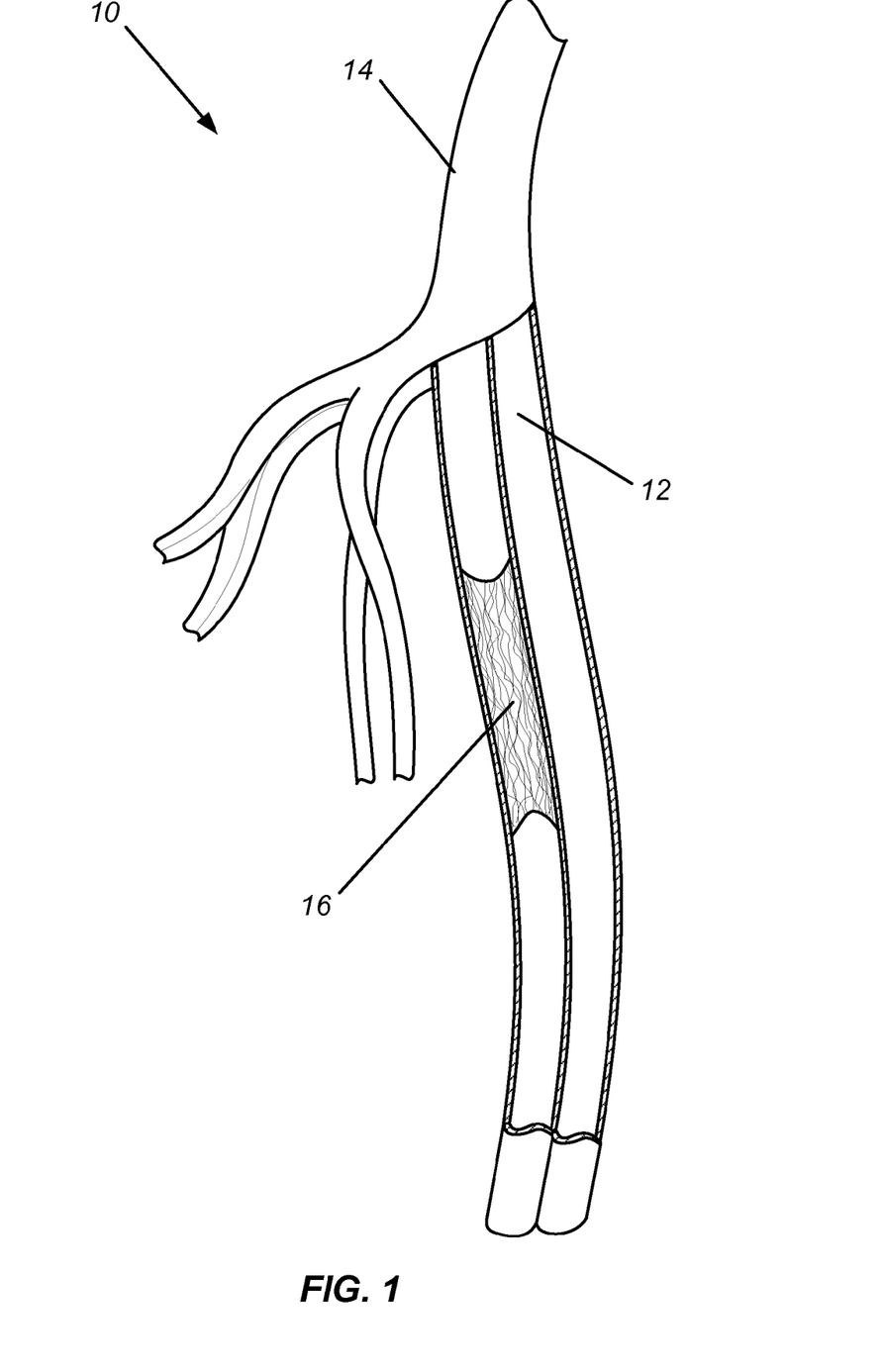
FIG. 1 is a partial cross-sectional view showing an obstructed artery, including the obstruction and the area adjacent both ends of the obstruction, and a vein alongside the artery, in accordance with various embodiments.

FIG. 1 is a simplified diagram of a portion of the peripheral vasculature 10 illustrating a vein 12 and an artery 14 having an obstruction or restriction 16 disposed therein. In such vasculature 10, if such a restriction 16 develops in artery 14, the delivery of oxygenated blood to the periphery (e.g., limb) distal to restriction 16 may be significantly compromised. Accordingly, it may be desirable to establish an alternative pathway for the oxygenated blood to flow to the periphery, for example using percutaneous bypass.

Figure 2:
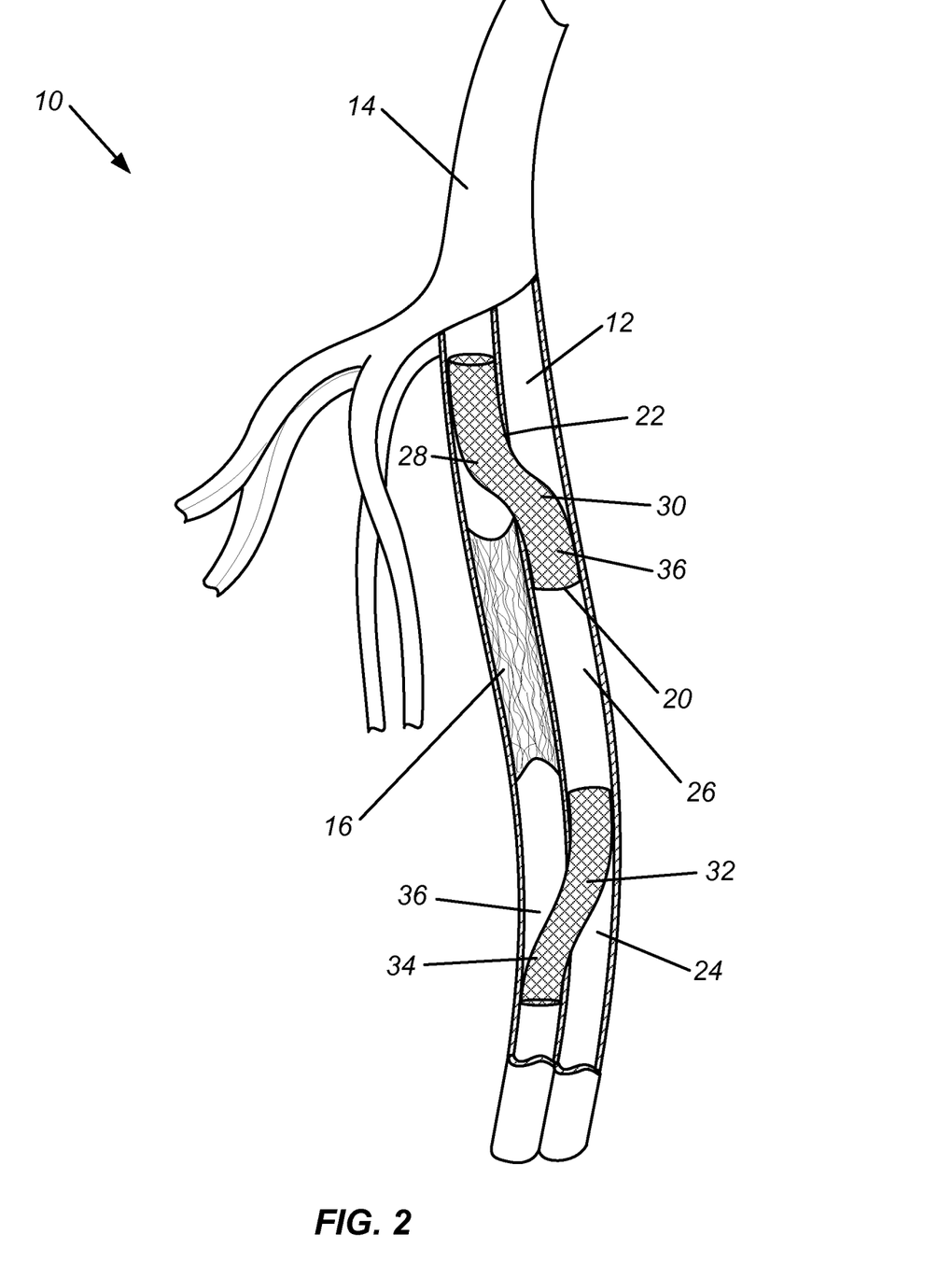
FIG. 2 illustrates a pair of temporary prop (non-covered) stents placed proximally and distally in an anastomosis created between the obstructed artery and adjacent vein shown in FIG. 1, in accordance with various embodiments.

With reference to FIG. 2, an alternative pathway 20 for blood flow may be established by a pair of arterial/venous (AV) fistulas 18, which may be in the form of a vascular graft or the like, and which may provide a route for the bloodflow to bypass restriction 16. In various embodiments, alternative pathway 20 may include a proximal end 22, a distal end 24 and a lumen 26 extending therethrough. In various embodiments, alternative pathway 20 may pass through arterial exit hole 28 and into venous entry hole 30, through a portion of vein 12, into venous exit hole 32, and out arterial re-entry hole 34 and back into artery 14. With this arrangement, blood flowing into artery 14 may flow into the proximal end 22 of pathway 20, through lumen 26, and may exit the distal end 24 of pathway 20, thus delivering oxygenated blood to the periphery. Thus, in various embodiments, pathway 20 may provide an alternative path for the oxygenated blood to flow around restriction 16. A detailed description of this technique is disclosed in International U.S. Pat. No. 7,374,567, which is hereby incorporated by reference.

Although the general method of bypassing a restriction in an artery by providing a conduit via an adjacent vein is known, the percutaneous transluminal technique may be particularly difficult from a device standpoint due to the potentially long distance between the vascular access site and the treatment site, the relatively small lumen size of the vascular path, and the precise control required for the technique in a dynamic environment. As used herein, the term "extravascular opening" may include any one or a combination of the following: an arterial entry or re-entry, an arterial exit, a venous entry or re-entry, and/or a venous exit. In a similar manner, the term "pathway" as used herein may include, without limitation, a pathway established external to an artery, internal to an artery, through an opening in an artery, and/or in the case of adjacent vessels, the pathway may be defined by the openings in the vascular wall(s) and passage through the vessel.

With reference to FIG. 2, in various embodiments, a general peripheral percutaneous transluminal bypass procedure may be described as follows. First, a suitable device may be navigated to the vasculature using conventional methods. For example, access to the site of the occlusion may be established by way of an artery, such as an ipsilateral or contralateral femoral artery, for example, using an access sheath and guide catheter navigated using a guidewire. Once the desired device is navigated to the treatment site proximal of restriction 16 in the artery 14, the treating physician may determine the correct penetration site to create an extravascular opening. In various embodiments, a tissue penetrating device then may create the extravascular opening in the vascular wall of artery 14, and may be further used to define a pathway to vein 12. In various embodiments, the process of creating the extravascular opening and the pathway may be monitored to ensure that a proper position for the extravascular opening and pathway are established.

In various embodiments, once the extravascular opening in artery 14 is established and a pathway to the vein 12 is defined, an extravascular opening may then be established in vein 12. In some embodiments, this may be accomplished utilizing the same tissue penetrating device. The creation of the extravascular opening in vein 12 may also be monitored to ensure that a proper venous access opening has been established. In various embodiments, after creating an opening in artery 14 and a pathway to an opening in vein 12, the openings and pathway may be maintained by a suitable means such as a vascular graft or stent 36 (e.g., a self-expanding or balloon-expandable stent). The stents and grafts will usually be intended for permanent implantation. In some instances, placeholder stents may be used before placement of a permanent stent or graft, where the placeholder may optionally be removed. This may establish fluid communication between artery 14 proximal of restriction 16 to vein 12, as illustrated in FIG. 2.

With reference to FIG. 2, in various embodiments, placeholder stent 36 may be a smooth, fairly flexible stent with a mild amount of tensile strength, such as a self-expanding, non-covered mesh (e.g. Nitinol™) stent. In some embodiments, placeholder stent 36 may be adapted to adopt an "S" curve from artery 14 into and across the anastomosis to vein 12. In particular embodiments, placeholder stent 36 may then adopt a second "S" curve distally from vein 12 and back into artery 14 after the return opening is established in vein 12 and artery 14 as described below, whereas in other embodiments a second "S" shaped placeholder stent 36 may be used for this purpose. In some embodiments, placeholder stent 36 may be biased to adopt the "S' shape, for example by varying the thickness of the mesh wall. For example, in one embodiment, placeholder stent 36 may be biased toward a modified "S" shape by shaping the wall of the stent along the convex curvature to be a little thinner (or having a single layer or thinner mesh weave, for example) and along the concave curvature a little thicker (or having a double layer or thicker mesh weave, for example) to cause the bias. In some embodiments, placeholder stent 36 may be further dilated with a differential dilation stent as described in more detail below.

In various embodiments, the next steps involve establishing a fluid path between vein 12 and artery 14 distal to restriction 16. This may be accomplished, in various embodiments, by creating an extravascular opening in vein 12, defining a pathway to artery 14, creating an extravascular opening in artery 14 distal to restriction 16, monitoring the progress of the creation of the extravascular openings and pathway, and providing a device, such as a placeholder stent 36, to maintain the fluid path once established.

Although this procedure is described herein in general terms, one of skill in the art will appreciate that the procedure may be modified for formation of an arterial/venous bypass in any part of the body, for example in an iliac bypass (e.g., a bypass spanning a blockage in an iliac artery), in a superficial femoral bypass (e.g., a bypass spanning a blockage in a superficial femoral artery), in a common femoral bypass (e.g., a bypass spanning a blockage in a common femoral artery), in a popliteal artery (e.g., a bypass spanning a blockage in a popliteal artery), in a posterior tibial bypass (e.g., a bypass spanning a blockage in a posterior tibial artery), in a perineal bypass (e.g., a bypass spanning a blockage in a perineal artery), or in an anterior tibial bypass (e.g., a bypass spanning a blockage in an anterior tibial artery). Approaches to such arteries are known to those of skill in the art, and may include any convenient artery that has a diameter that is sufficiently large to admit the catheters, stents, and guidewires required for the procedure. In some embodiments, the blockage may be accessed via an ipsilateral or contralateral femoral artery.

Figure 3:
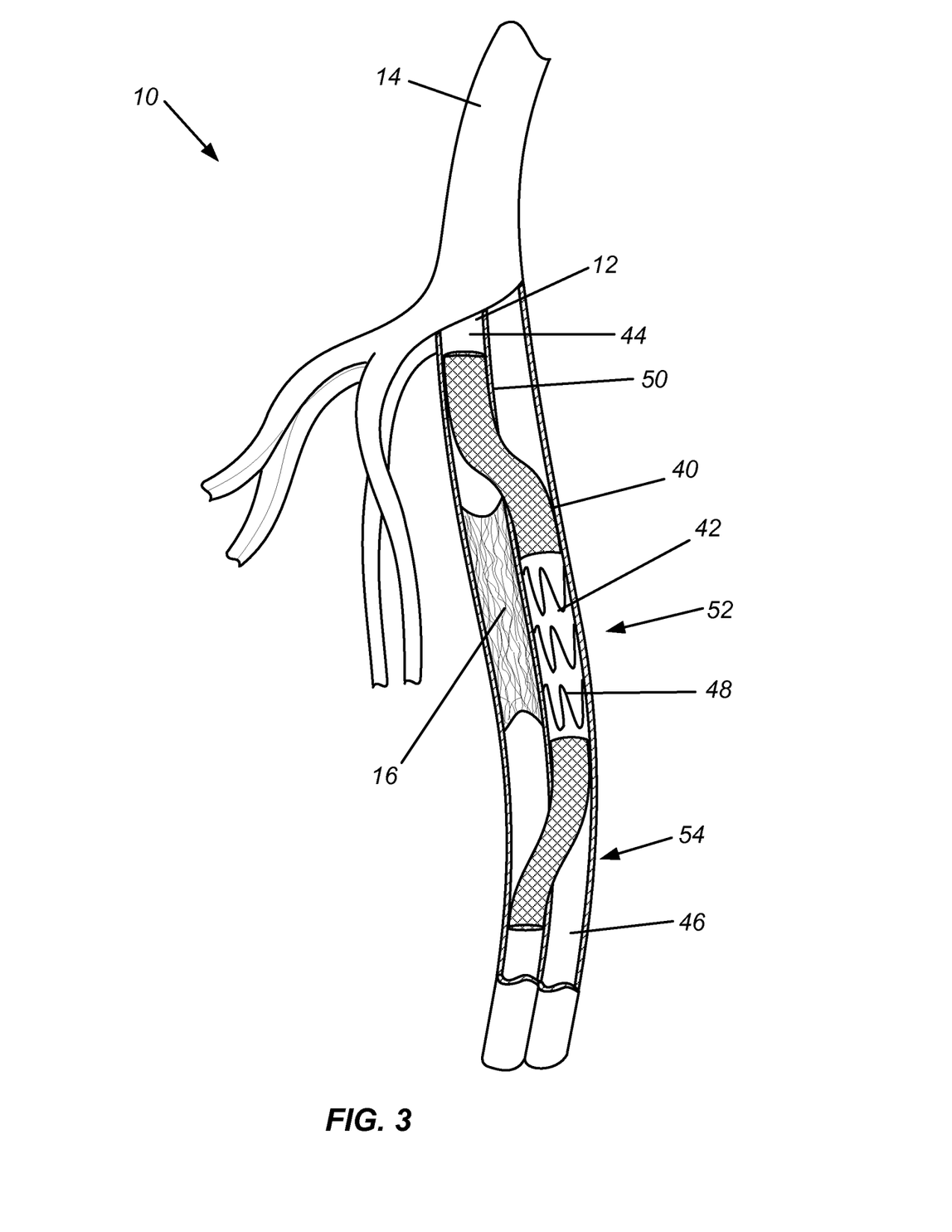
FIG. 3 illustrates a differential dilation self-expanding stent placed inside the temporary stents shown in FIG. 2 and bridging a bypass between the artery and vein graft, in accordance with various embodiments.

In various embodiments, the device provided to maintain the fluid path once established using the placeholder stent may be a differential dilation stent as described herein. FIG. 3 illustrates an example of such a differential dilation stent 40 in use spanning an arterial occlusion 16. As shown in FIG. 3, differential dilation stent 40 may include a self-expanding mesh structure 42 having a generally cylindrical shape that is configured to contact an interior lining or wall of artery 14 and/or vein 12 when expanded. In various embodiments, differential dilation stent 40 may include a film layer on both the inside and outside surfaces, which, in some examples, may be made of a flexible material such as polytetrafluoroethylene (PTFE) or ultra high molecular weight polyethylene (UHMWPE), for example. In various embodiments, differential dilation stent 40 may have a nominal shape that is generally cylindrical, including first (proximal) and second (distal) opposed ends 44, 46 communicating with an interconnecting central lumen 48. The inner and outer film layers may be substantially the same length and may be connected or sealed together, particularly adjacent ends 44, 46. In some embodiments, mesh layer 42 may be shorter in length than the inner and outer film layers, for example by about 0.5 mm, although is some embodiments mesh layer 42 may be substantially the same length as the inner and outer film layers.

In various embodiments, when extended, differential dilation stent 40 may have a length from first (proximal) end 44 to second (distal) end 46 of from about 20 cm to about 150 cm, or even longer, for instance depending on the anatomy of the patient, and may have a diameter of about 2 mm-12 mm in various regions or portions, depending on the anatomy of the patient, the site of the occlusion, and the particular artery and/or vein. In some embodiments, differential dilation stent 40 also may include two or more different regions, such as a proximal region 50, a central region 52, and a distal region 54. In various embodiments, the diameter, length, and tensile strength (e.g., flexibility, firmness, and/or expansion force) of each region may be individually configured to suit a particular medical use. For example, differential dilation stent 40 may be configured to have more tensile strength and a greater diameter proximally near the site of the anastomosis (e.g., in proximal region 50) and less tensile strength and a larger diameter centrally near the vein graft (e.g., in central region 52) where the diameter of the vessel is larger and the vessel walls are more compliant. In some embodiments, distal region 54, which re-enters and passes through artery 14, may have a tensile strength similar to that of proximal region 50, but may have a smaller diameter than central region 52. In some embodiments, having a more compliant, softer, and/or flexible central region 52 may reduce the likelihood of damage to and reduces stress on vein 12, which may have more compliant walls than artery 14. Conversely, in some embodiments, having a less compliant, more rigid proximal or distal end may help with directing differential dilation stent 40 through the vessel walls and may retain the anastomosis in an open configuration.

Conventional self-expanding stents normally expand to fit the dimensions of the vessel they are seated in, but in various embodiments, the stents of the present disclosure may not necessarily expand all of the way to span the inner walls of the vessel. For example, in one embodiment, differential dilation stent 40 may have a proximal region 50 that is about 4-10 mm in diameter and about 10-30 cm in length, while distal region 54 may be about 2-8 mm in diameter and may be about 10-20 cm long. In this embodiment, central region 52 may have a diameter of about 5-12 mm, and may have a length of about 20-100 cm in length.

In one specific, non-limiting embodiment, for example, for a femoral-popliteal bypass, differential dilation stent 40 may have an overall length of about 80 cm, for example, a proximal region 50 with a diameter of about 6-8 mm, for example, about 7 mm, a central region 52 with a diameter of about 5-12 mm, for example, about 8 mm, and a distal region 54 with a diameter of about 4-6 mm, for example, about 5 mm.

In another specific, non-limiting embodiment, for example, for a femoral-tibial bypass, differential dilation stent 40 may have an overall length of about 55-65 cm, for example, about 60 cm, a proximal region 50 with a diameter of about 5-7 mm, for example, about 6 mm, a central region 52 with a diameter of about 5-12 mm, for example, about 8 mm, and a distal region 54 with a diameter of about 2-4 mm, for example, about 3 mm.

In many embodiments, it will be desirable that the portion of the stent or graft in the vein have a diameter which is less than that of the vein so that a portion of the venous lumen remains available for normal venous blood flow.

The tensile strength or expansion force of differential dilation stent 40 in different regions (e.g., proximal, central, and distal) may be controlled in several ways, in accordance with various embodiments. For example, the thickness of the nitinol wire used to weave the wire mesh layer of differential dilation stent 40 may be varied, with a thinner wire used in more compliant regions (e.g., central region 52), and a thicker wire used in less compliant regions (e.g., proximal and distal regions 50, 54) in some embodiments. Alternately or additionally, the wire mesh may be formed from a more expandable pattern or a double weave in more compliant regions (e.g., central region 52), and a less expandable pattern in more compliant regions (e.g., proximal and distal regions 50, 54) in accordance with various embodiments. Further, in some embodiments, the wire mesh layer may be formed using two or more different materials with different inherent resistances to expansion, for example incorporating a blend of nitinol and steel in the less compliant regions (e.g., proximal and distal regions 50, 54).

In some embodiments, differential dilation stent 40 may be adapted to automatically adopt an "S" curve (or other curved shape) from the artery into and across the anastomosis to the vein. In particular embodiments, differential dilation stent 40 may be adapted to then adopt a second "S" curve distally from the vein and back into the artery after the return opening is established in the vein 12 and artery 14. In some embodiments, differential dilation stent 40 may be biased to adopt the "S" shape (or other curve), for example by varying the thickness of the mesh wall. For example, in one embodiment, the placeholder stent may be biased toward a modified "S" shape by shaping the wall of the stent along the convex curvature to be a little thinner and along the concave curvature a little thicker to cause the bias.

Figure 4:
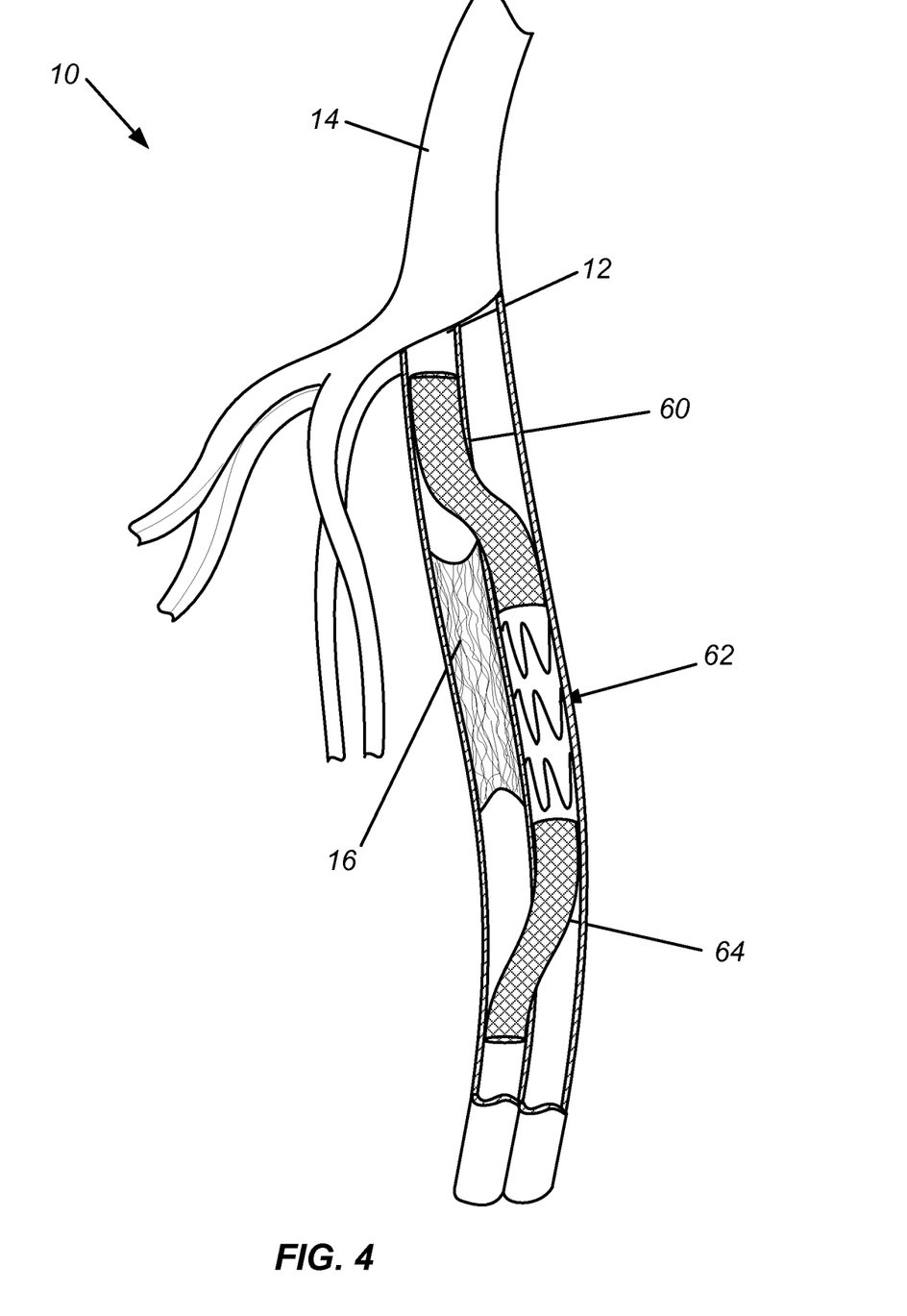
FIG. 4 illustrates a modular differential dilation self-expanding stent placed inside the temporary stents shown in FIG. 2 and bridging a bypass between the artery and vein graft, in accordance with various embodiments.

In other embodiments, as illustrated in FIG. 4, a set of modular stents (e.g., proximal stent 60, central stent 62, and distal stent 64) may be used in place of the single differential dilation stent 40 described above. In various embodiments, the dimensions and/or tensile strength of proximal stent 60, central stent 62, and distal stent 64 may generally correspond to the tensile strength and/or dimensions of proximal 50, central 52, and distal 54 regions of differential dilation stent 40 as described above. In various embodiments, two firmer modular stents 60, 64 may be placed proximally and distally of restriction 16, respectively, and connecting artery 14 to vein 12 on both sides of the restriction 16, and then vein 12 may receive a more compliant stent 62, for example made of PTFE or Dacron, to reduce or eliminate stretching of vein 12.

In various embodiments, modular stents 60, 62, and 64 may be placed with or without placeholder stents 36. In various embodiments, proximal stent 60, which may have a high tensile strength (e.g., it may be highly reinforced to maintain the proximal anastomosis) it may have an expanded diameter of about 5-10 mm, or about 7 mm in some examples. In various embodiments, because central stent 62 may be positioned within the more compliant vein, it may be more compliant (e.g., have a lower tensile strength) like central portion 52 of differential dilation stent 40. In various embodiments, central stent 62 may have an expanded diameter of from about 5 mm to about 12 mm. The length of central stent 62 may be from about 20 cm to as much as 80 cm or even 100 cm in some embodiments. In various embodiments, distal stent 64 may be reinforced (e.g., have a high tensile strength) since it may pass through and maintain the distal anastomosis, and may have an expanded diameter of from about 3 mm to about 8 mm, or about 5 mm in certain examples. Distal stent 64 also may have a length of about 10 cm to 20 cm in length.

In further embodiments, differential dilation stent 40 (or modular stents 60, 62, 64) may be provided with one or more radiopaque portions, for example, adjacent first and second ends 44, 46. Thus, in some embodiments, after differential dilation stent 40 (or modular stents 60, 62, 64) has been installed and expanded in a human blood vessel, differential dilation stent 40 (or modular stents 60, 62, 64) may be observed under an X-ray and the relative locations of ends 44, 46 may be determined.

Figure 5:
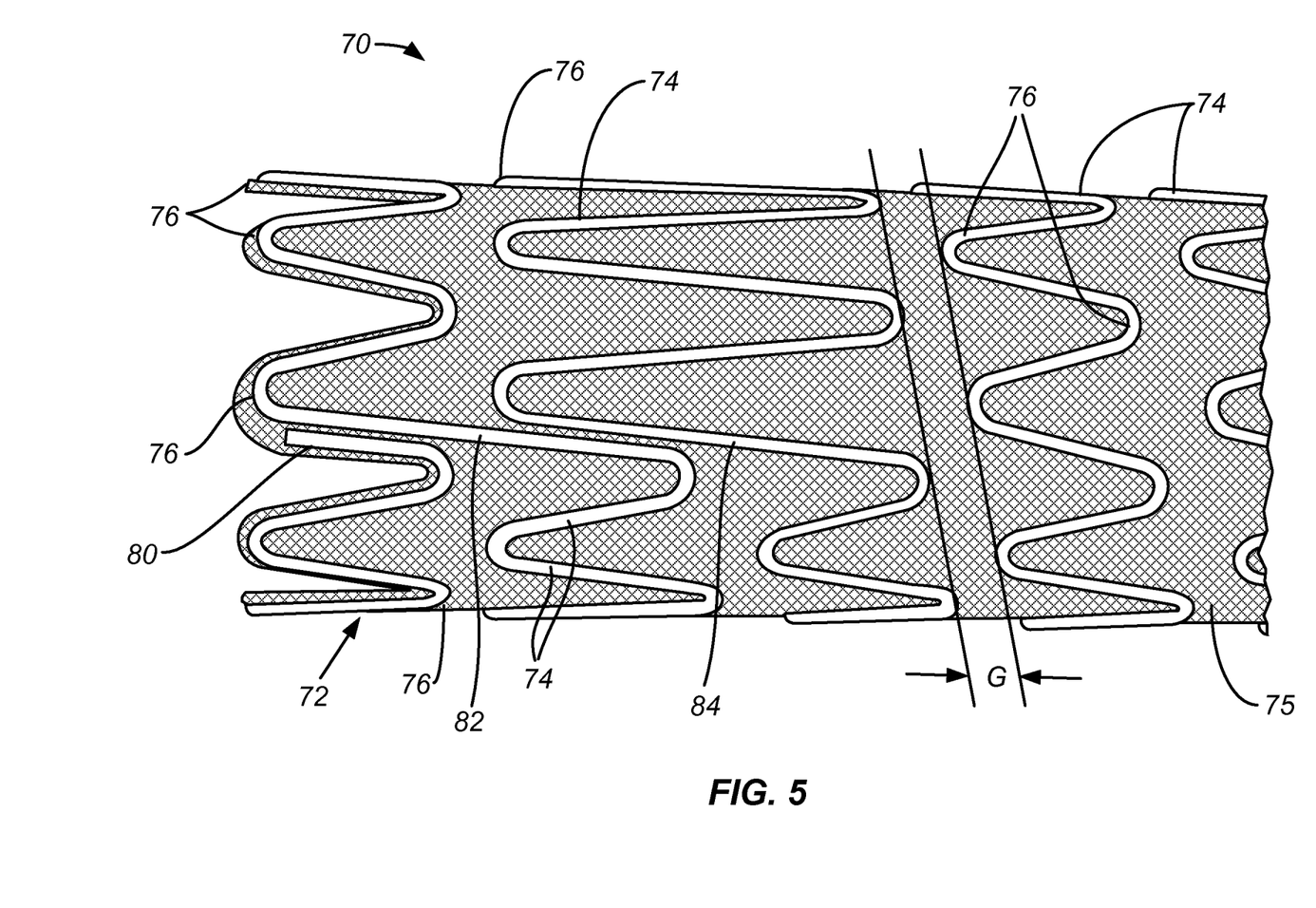
FIG. 5 illustrates a detail of an exemplary stent scaffold construction in accordance with the present invention.

Referring now to FIG. 5, a stent 70 comprises a stent body 72 in the form of a plurality of serpentine rings each including axial struts 74 joined by arcuate joints 76. Although the rings will be referred to individually, they will usually comprise a continuous helical structure with only one distal end and one proximal end, particularly when they are formed as a bent wire. When formed by laser cutting, the rings could be independent but will usually be a continuous helical structure. The serpentine rings are disposed between at least one inner membrane or a layer 75 of a graft material and at least one outer layer (not shown), where the inner and outer layers are joined together to encapsulate the scaffold structure 72. At at least one end of the stent 70, the layers of graft material 75 will usually be "scalloped" so that the graft terminates in an undulating pattern which matches the pattern of the terminal serpentine ring.

In order to enhance the radial strength (hoop strength) of the scaffold structure 72 at at least one end (and preferably at both ends), the tail strut 80 may be welded or otherwise attached to the adjacent strut 82. To further enhance the strength of this end, the adjacent strut 82 may have a length sufficient to span the terminal ring as well as the adjacent ring which is one position inward from the terminal layer. This strut 82 will preferably be joined to the adjacent strut 84, and strut 84 itself may be lengthened to transition into the remainder of the serpentine rings.

Except for the struts 82 and 84 which span adjacent serpentine rings structures, there will usually be a gap G maintained between the arcuate ends 74 of the adjacent serpentine rings. This gap will be maintained within the ranges discussed above in order to enhance bendability of the stent structure while maintaining sufficient radial or hoop strength.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A stent configured for insertion in a human blood vessel, the stent comprising: a compressible, self-expanding, substantially cylindrical body comprising a plurality of serpentine rings including a terminal ring at one end of the body and an adjacent ring inward from the terminal ring, wherein each serpentine ring comprises a plurality of axial struts wherein circumferentially adjacent-struts are joined by arcuate joints and wherein each serpentine ring has having an inside surface, an outside surface, a proximal end, and a distal end, and wherein at least some of the axially adjacent serpentine rings other than the terminal ring and inward ring maintain a longitudinal gap between ends of adjacent arcuate joints; and a flexible coating including at least one sheet or membrane covering each surface of the body in order to fully encapsulate the body, wherein at least one strut other than a tail strut the terminal ring is longer than all other struts in the terminal ring and has a length sufficient to span the terminal ring and the adjacent ring inward from the terminal ring to create an overlap which enhances the strength of the ends of the body; wherein the cylindrical body comprising a single continuous bent wire with only one distal end and one proximal end formed into a continuous helical structure.

2. The stent of claim 1, wherein the flexible coating comprises polytetrafluoroethylene (PTFE).

3. The stent of claim 1, wherein the cylindrical body comprises nickel titanium alloy.

4. The stent of claim 1, wherein the cylindrical body has a length in the range from about 40 cm to about 150 cm.

5. The stent of claim 1, wherein the cylindrical body is biased toward an open position.

6. The stent of claim 1, wherein the cylindrical body is biased toward a curved position.

7. The stent of claim 6, wherein the curved position comprises a substantially S-shaped curve.

8. The stent of claim 6, wherein the curved position comprises two substantially S-shaped curves.

9. The stent of claim 8, wherein a first substantially S-shaped curve is located near the proximal end, and wherein a second substantially S-shaped curve is located near the distal end.

10. The stent of claim 1, wherein the tail wire is attached along its length to the at least one strut.

11. The stent of claim 10, wherein the at least one strut is attached to a strut in the adjacent ring which strut spans a third ring.

12. The stent of claim 1, wherein small holes are formed through the flexible coating.

13. The stent of claim 1, wherein the holes are laser drilled and have a diameter in the range from 5 microns to 30 microns.

14. The stent of claim 1, wherein at least one of the insider and the outside of the flexible coating comprises a drug.

15. The stent of claim 14, wherein the drug comprises heparin and the heparin is non-releasably formed on the flexible coating.

16. The stent of claim 1, wherein said at least one strut is attached to an adjacent strut.

17. The stent of claim 1, wherein the flexible coating comprises an ultra high molecular weight polyethylene (UHMWPE) material.

* * * * *